US007220413B2

(12) United States Patent
Ferguson

(10) Patent No.: US 7,220,413 B2
(45) Date of Patent: May 22, 2007

(54) PHARMACEUTICAL COMPOSITION CONTAINING INHIBITORS OF INTERFERON-γ

(75) Inventor: Mark William James Ferguson, Cheshire (GB)

(73) Assignee: Renovo Limited, Manchester (GB)

( * ) Notice: Subject to any disclaimer, the term of this patent is extended or adjusted under 35 U.S.C. 154(b) by 0 days.

(21) Appl. No.: 11/014,209

(22) Filed: Dec. 17, 2004

(65) Prior Publication Data

US 2005/0158319 A1 Jul. 21, 2005

Related U.S. Application Data

(63) Continuation of application No. 09/790,898, filed on Feb. 23, 2001, now abandoned, which is a continuation of application No. 09/029,098, filed as application No. PCT/GB96/01949 on Aug. 9, 1996, now abandoned.

(30) Foreign Application Priority Data

Aug. 18, 1995 (GB) ................................ 9516967.8

(51) Int. Cl.
*A61K 39/395* (2006.01)

(52) U.S. Cl. ................................ 424/158.1; 424/145.1

(58) Field of Classification Search ..................... None
See application file for complete search history.

(56) References Cited

U.S. PATENT DOCUMENTS

| | | | |
|---|---|---|---|
| 4,897,264 | A | 1/1990 | Novick et al. |
| 5,124,147 | A | 6/1992 | Wissner et al. |

FOREIGN PATENT DOCUMENTS

| | | | |
|---|---|---|---|
| EP | 0 304 291 | A | 2/1989 |
| EP | 304291 | A | 2/1989 |
| EP | 328255 | A | 8/1989 |
| EP | 0 369 413 | | 5/1990 |
| EP | 0 387 095 | | 9/1990 |
| EP | 0 393 502 | | 10/1990 |
| EP | 0 416 652 | | 3/1991 |
| EP | 0 528 469 | A | 2/1993 |
| EP | 528469 | A | 2/1993 |
| WO | 8807869 | A | 10/1988 |
| WO | WO 88/07869 | * | 10/1988 |
| WO | 91 02005 | A | 2/1991 |
| WO | 92 06115 | A | 4/1992 |
| WO | WO 94/12531 | | 6/1994 |
| WO | WO 94/14467 | | 7/1994 |
| WO | WO 95/16036 | | 6/1995 |

OTHER PUBLICATIONS

Pittet et al. Plast Reconstr Surg., 1994; 93: 1224-35.*
Miles et al. J Surg Res., 1994; 56: 288-94.*
Ziesche and Block. Wien Klin Wochenschr., 2000; 112: 785-90.*
Hulten. Am J Surg., 1994; 167: 42S-45S.*
Granstein et al, "A Controlled Trial of Intralesional Recombinant Interferon-γ in the Treatment of Keloidal Scarring", Arch. Dermatol. 126:1295-1302 (1990).

* cited by examiner

*Primary Examiner*—Elizabeth Kemmerer
*Assistant Examiner*—Christina Borgeest
(74) *Attorney, Agent, or Firm*—Nixon & Vanderhye P.C.

(57) ABSTRACT

The present invention provides compositions and methods for promoting the healing of wounds or fibrotic disorders with reduced scarring, comprising inhibitors and inhibiting IFN-γ, together with compositions and methods for promoting the healing of chronic wounds, comprising stimulating and stimulators of IFN-γ.

9 Claims, No Drawings

PHARMACEUTICAL COMPOSITION CONTAINING INHIBITORS OF INTERFERON-γ

This application is a continuation of the U.S. application Ser. No. 09/790,898, filed Feb. 23, 2001, now abandoned which is a continuation of U.S. application Ser. No. 09/029,098, filed May 13, 1998, now abandoned which is the U.S. national phase of international application PCT/GB96/01949, filed on Aug. 9, 1996, which designated the U.S. and claims priority to GB Application No. 9516967.8, filed Aug. 18, 1995. The entire contents of these applications are incorporated herein by reference.

The present invention concerns pharmaceutical preparations for promoting the healing of wounds or fibrotic disorders, in particular for promoting the healing of wounds or fibrotic disorders with reduced scarring, and for promoting the healing of chronic wounds.

By "wounds or fibrotic disorders" is meant any condition which may result in the formation of scar tissue. In particular, this includes the healing of skin wounds, the repair of tendon damage, the healing of crush injuries, the healing of central nervous system (CNS) injuries, conditions which result in the formation of scar tissue in the CNS, scar tissue formation resulting from strokes, and tissue adhesion, for example, as a result of injury or surgery (this may apply to e.g. tendon healing and abdominal strictures and adhesions). Examples of fibrotic disorders include pulmonary fibrosis, glomerulo-nephritis, cirrhosis of the liver, and proliferative vitreoretinopathy.

In particular, there is a lack of compositions for promoting the healing of wounds or fibrotic disorders with reduced scarring. Scar tissue formation, although providing mechanical strength to a healed wound, can be unsightly and may impair the function of the tissue.

This is particularly the case in wounds which result in scar tissue formation in the CNS, the scar tissue inhibiting the reconnection of severed or re-growing nerve ends, so significantly affecting their function.

There is also a lack of compositions for use in the treatment of chronic wounds, for example venous ulcers, diabetic ulcers and bed sores (decubitus ulcers). especially in the elderly and wheel chair bound patients. Such compositions may be extremely useful in patients where wound healing is either slow or in whom the wound healing process has not vet started. Such compositions may be used to "kick-start" wound healing and may then be used in combination with compositions (e.g. those of PCT/GB93/00586) which promote the healing of wounds or fibrotic disorders with reduced scarring. Hence not only may a chronic wound be healed, but it may be healed with reduced scarring.

According to the present invention there is provided an inhibitor of IFN-γ (Interferon-γ) for use in promoting the healing of wounds and fibrotic disorders with reduced scarring.

IFN-γ (Type II or immune interferon) is produced primarily by T lymphocytes upon mitogen or antigen stimulation (Trinchieri et al., 1985, Immunology Today, 6: 131). IFN-γ (both murine and human) exert their effects through specific, saturable, binding to a single class of high affinity receptors found on a variety of cells including fibroblasts, endothelial cells and monocytes/macrophages.

IFN-γ has been widely studied (see, for example, Kovacs, E. J., 1991, Immunology Today, 12(1): 17–23—who states that IFN-γ decreases fibroblast proliferation and connective tissue production, i.e. inhibits scar tissue formation). Past studies of the effects of IFN-γ at wound sites have shown (Pittel, B. et al., 1994, Plastic and Reconstructive Surgery, 93: 1224–1235) that in studies on the effect of intralesional injection of IFN-γ to hypertrophic scars (an abnormal thickening of muscle), most (6/7) patients showed relief of symptoms, and all patients showed reduced lesion size during treatment, although there was no change in the total collagen content. Duncan et al (1985, J. Exp. Med., 162: 516–527) and Amento et al (1985, J. Clin. Invest., 76: 836–848) have shown that IFN-γ inhibits collagen types I and III and fibronectin synthesis by dermal and synovial fibroblasts and collagen type II by chondrocytes in a dose-dependent manner. Murray et al (1985, J. Immunol., 134: 1619–1622) have also shown that IFN-γ is involved in macrophage activation in vivo. Tamai et al (1995, J. Invest. Dermatol., 104: 384–390) have shown that IFN-γ is involved in the regulation of metalloproteases (MMP) and tissue inhibitor of metalloproteases (TIMP) in in vitro cell culture. Various uses for IFN-γ and antagonists of same are proposed in EP 0304291, EP 0528469, WO 92/06115, WO 91/02005, WO 88/07869, EP 0328255, WO 92/14480, WO 87/07842, WO 94/07497, and Lorat-Jacobs, H. et al., 1994, Path. Res. Pract. 190: 920–922.

It appears that IFN-γ is a multi-potent molecule with many actions depending on the conditions of the environment to which it is added. Several groups have reported decreased collagen synthesis in vitro on addition of IFN-γ to cultures, and Granstein et al (1989, J. Invest. Dermatol., 93: 18–27) have shown inhibition of collagen deposition and hence healing with reduced scarring in wounds treated with IFN-γ. From these results, it appears that the treatment of sites (of wounds or fibrotic disorders) with IFN-γ would result in healing with reduced scarring.

Experiments undertaken (see 'Experimental' section below) have shown that, very surprisingly, the inhibition of IFN-γ actually promotes healing with reduced scarring, despite the teachings of the prior art.

The inhibitor may, for example, be a neutralising antibody. It may be a monoclonal antibody, a polyclonal antibody, a phage-derived antibody, a genetically engineered antibody (e.g. diabody), or antibody derived from a transgenic mouse.

Alternatively, the inhibitor may be anything which inhibits IFN-γ from interacting with its receptor (i.e. antagonises IFN-γ receptor activation) or which inhibits the receptor's activation. It may, for example, be a molecule which mimics the IFN-γ receptor binding sequence and which binds to the receptor but does not activate it, thereby competitively inhibiting the binding of IFN-γ to the receptor and inhibiting the activation of the receptor.

The inhibitor may be used in conjunction with a pharmaceutically acceptable carrier, diluent or excipient.

The inhibitor may be used in conjunction with a composition for promoting the healing of wounds or fibrotic disorders with reduced scarring.

The inhibitor may be used in conjunction with a composition for promoting the healing of chronic wounds.

Also provided according to the present invention is a method for promoting the healing of wounds or fibrotic disorders with reduced scarring comprising inhibiting IFN-γ.

The inhibition may be achieved by administering to a site an inhibitor of IFN-γ. By "site" is meant a site of wounding or fibrotic disorder. The inhibitor may be an inhibitor according to the present invention.

Between about 300 and about 30,000 IU IFN-γ may be inhibited.

The IFN-γ may be inhibited immediately prior to wounding/onset (by "onset" is meant the onset of a fibrotic disorder). It may be inhibited immediately after wounding/onset, although it may also be inhibited later, for example within approximately 3 or 7 days of wounding/onset.

The method may be used in conjunction with a method for promoting the healing of wounds or fibrotic disorders with reduced scarring.

The method may be used in conjunction with a method for promoting the healing of chronic wounds.

According to a further aspect of the present invention there is also provided a stimulator of IFN-γ for use in promoting the healing of chronic wounds.

The experiments (see 'Experimental' section below) have also shown that, very surprisingly, treatment of a site with IFN-γ actually promotes the deposition of collagen and healing with increased scarring and therefore may be used to promote the healing of chronic wounds.

By "stimulator" is meant anything which may stimulate (i.e. agonise) the quantity or efficacy of active IFN-γ at a site or the activation of the IFN-γ receptor. This may be IFN-γ itself or partially modified form of IFN-γ. A partially modified form of IFN-γ may, for example, have a longer half-life than IFN-γ. Alternatively, it may be an inhibitor of IFN-γ metabolism.

Partial modification may be by way of addition, deletion or substitution of amino acid residues. A substitution may for example be a conserved substitution. Hence a partially modified molecule be a homologue of the molecule from which it was derived. It may have at least 40%, for example 50, 60, 70, 80, 90 or 95%, homology with the molecule from which it is derived.

The stimulator may be used in conjunction with a pharmaceutically acceptable carrier, diluent or excipient.

The stimulator may be used in conjunction with a composition for promoting the healing of wounds or fibrotic disorders with reduced scarring.

The stimulator may be used in conjunction with a composition for promoting the healing of chronic wounds.

Also provided according to the present invention is a method for promoting the healing of chronic wounds comprising stimulating IFN-γ at a site. By "stimulating" is meant increasing the quantity or efficacy of active IFN-γ at a site or the activation of the IFN-γ receptor.

The stimulation may be achieved by administering to a site a stimulator of IFN-γ. The stimulator may be a stimulator according to the present invention.

Between about 7,500 and 15,000 IU IFN-γ may be administered to stimulate a site.

The IFN-γ may be stimulated immediately prior to wounding. It may be stimulated immediately after wounding, although it may also be stimulated later, for example within approximately 3 or 7 days or longer of wounding.

The method may be used in conjunction with a method for promoting the healing of wounds or fibrotic disorders with reduced scarring.

The method may be used in conjunction with a method for promoting the healing of chronic wounds.

The invention will be further apparent from the following example which shows, by way of example only, forms of inhibition of IFN-γ and promotion of healing with reduced scarring, and of promotion of healing of chronic wounds.

EXPERIMENTAL

Method 84 male CD1 mice, 12 to 15 weeks old (Charles River) were anaesthetised using equal parts halothane, oxygen and nitrous oxide. 2×1 cm full-thickness incisions (through the panniculus carnosus) were made 3 cm from the base of the skull and 1 cm either side of the dorsal midline.

Test solutions used were anti-IFN-γ, IFN-γ and PBS. Anti-IFN-γ comprised monoclonal antibody against murine IFN-γ (MuIFN-γ;=rat IgG'2a). Antibodies were obtained as ascites fluid from thymusless nude-mice innoculated with the F3 hybridoma clone (J. Immunol., 1987, 138: 4178) and purified by affinity chromatography on an anti-rat kappa-chain mAb. The neutralisation potential of the antibody was 1/1,000,000 against 30 U/ml of MuIFN-γ and contained 1.25 ng/ml endotoxin. IFN-γ was Chinese hamster ovary (CHO) cell-derived reconbinant MuIFN-γ purified by affinity chromatography on anti-IFN-γ mAb. The IFN-γ was at an initial concentration of 300,000 IU/ml (endotoxin: 73 pg/ml).

Animals were split into several groups as follows:

Group A: Animals were treated with a single intraperitonal (IP) injection (100 μl) of neat anti-IFN-γ antibodies prior to wounding.

Group B: Animals were treated with a single intradermal (ID) injection of 50 μl or 25 μl of anti-IFN-γ antibodies (diluted with PBS) prior to wounding.

Group C: Animals were treated with a single ID injection of IFN-γ (15,000 or 7,500 IU) prior to wounding.

Group D: Animals were treated with ID injections of IFN-γ (15,000 or 7,500 IU) on day 0 prior to wounding and days 3 and 7 post-wounding.

Group E: Animals were treated with a single control IP injection of PBS (phosphate buffered saline) on day 0 prior to wounding (control).

Group F: Animals were treated with a single control ID injection of PBS on day 0 prior to wounding.

Group G: Animals were treated with an ID injection of PBS on day 0 prior to wounding and days 3 and 7 post-wounding.

Animals were killed by chloroform overdose on days 7, 14, 70 & 120 post-wounding. Wounds were excised and bisected for routine histology and immunocytochemistry. 7 μm wax sections were cut and stained for Haemotoxylin and Eosin to assess cell invasion and re-epithelialisation, and for Masson's Trichome to assess collagen deposition and orientation.

Results

Anti-IFN-γ Antibodies:

No difference was observed between control wounds and treated wounds at any time point in the animals treated with a single IP injection.

With a single ID injection of anti-IFN-γ, there were no differences compared to controls at 7 and 14 days. However, by 70 and 120 days, marked differences in the orientation of the collagen fibres within the treated wound were observed.

Anti-IFN-γ treatment is anti-scarring, improving the quality of dermal architecture, despite the prior art observations. While the fibres were still relatively small and compacted immediately under the epidermis, they are randomly orientated, whereas in the mid and deep dermis the collagen fibres were less compacted and were orientated in a "basketweave" fashion. Control wounds (scarred) had compacted parallel collagen fibres throughout the wound area.

IFN-γ

At the early time points (7 and 14 days), all the IFN-γ-treated wounds (in both injection regimes) showed increased inflammation and angiogenesis in a dose-dependent manner, i.e. lower doses, although worse than control wounds, were not as bad as wounds treated with higher doses of IFN-γ.

By 70 and 120 days, the wounds treated on days 0, 3 and 7 post-wounding with a high dose of IFN-γ showed marked fibrosis (i.e. scarring). Macroscopically, the wounds were raised and, microscopically, densely packed collagen in large swirling bundles within the wound margins was observed. These treated wounds also showed residual inflammation at the base of the wound, compared to control wounds. Again, this scarring was dose-dependent, i.e. the greater the dose of IFN-γ, the greater the scarring.

Discussion

Previous work has shown that administration of IFN-γ to wounds inhibits collagen synthesis, suggesting that it may be useful as an anti-scarring agent. Other workers have shown that treatment of keloids or hypertrophic scars with IFN-γ decreases the size of the scar.

Contrary to these findings, these experiments have shown that, very surprisingly, the early treatment of wounds with IFN-γ causes fibrosis with raised scars that are packed full of collagen, whereas treatment of incisional wounds with antibodies to IFN-γ results in improved healing with collagen fibres orientated in a "basketweave" fashion resembling normal dermis (i.e. scarring is reduced).

The invention claimed is:

1. A method for improving healing of dermal wounds, the method comprising administering by intradermal injection to a patient in need of such improved healing an amount of an anti-interferon-γ (IFN-γ) antibody sufficient to alter the orientation of collagen fibres within the treated wound and thereby reducing scarring.

2. The method according to claim 1, wherein the anti-IFN-γ antibody is administered immediately prior to dermal wounding.

3. The method according to claim 1, wherein the anti-IFN-γ antibody is administered immediately after dermal wounding.

4. The method according to claim 1, wherein the anti-IFN-γ antibody is a neutralizing antibody.

5. The method according to claim 1, wherein the anti-IFN-γ antibody is selected from the group consisting of a monoclonal antibody, and polyclonal antibody, a phage-derived antibody, a genetically engineered antibody and an antibody derived from a transgenic mouse.

6. The method according to claim 1, wherein the anti-IFN-γ antibody prevents IFN-γ interacting with its receptor.

7. The method according to claim 1, wherein the anti-IFN-γ antibody is used in conjunction with a pharmaceutically acceptable carrier, diluent or excipient.

8. The method according to claim 1, wherein the anti-IFN-γ antibody is used in conjunction with a further agent that promotes the healing of wounds with reduced scarring.

9. The method according to claim 1, wherein the anti-IFN-γ antibody is used in conjunction with a further agent that promotes the healing of chronic wounds.

* * * * *